United States Patent [19]

Jasne et al.

[11] Patent Number: 5,153,303
[45] Date of Patent: Oct. 6, 1992

[54] POLYIMIDES PREPARED FROM DISUBSTITUTED AROMATIC TETRACARBOXYLIC ACID DIANHYDRIDES

[75] Inventors: Stanley J. Jasne, Peekskill; Pasquale A. Falcigno, Yonkers, both of N.Y.

[73] Assignee: Ciba-Geigy Corporation, Ardsley, N.Y.

[21] Appl. No.: 467,710

[22] Filed: Jan. 19, 1990

[51] Int. Cl.⁵ .................. C08G 69/26; C08G 69/42; C08G 75/00
[52] U.S. Cl. .................. 528/353; 204/142.36; 428/483.5; 430/9; 528/26; 528/27; 528/28; 528/125; 528/128; 528/188; 528/352
[58] Field of Search ............. 528/353, 125, 128, 188, 528/352, 26, 27, 28, 32, 229; 430/9; 428/473.5; 204/192.36

[56] References Cited

U.S. PATENT DOCUMENTS

| | | | |
|---|---|---|---|
| 3,856,752 | 12/1974 | Bateman et al. | 528/353 |
| 3,890,272 | 6/1975 | D'Alelio | 528/352 |
| 4,578,166 | 3/1986 | Uno et al. | 528/229 |
| 4,816,115 | 3/1989 | Horner et al. | 204/192.36 |
| 4,851,506 | 7/1989 | Rohde et al. | 528/35.3 |
| 4,914,181 | 4/1990 | Pfeifer et al. | 528/352 |

FOREIGN PATENT DOCUMENTS 59-161368 9/1984 Japan.

Primary Examiner—John Kight, III
Assistant Examiner—T. Mosley
Attorney, Agent, or Firm—JoAnn Villamizar

[57] ABSTRACT

Fully cyclized polyimides based on aromatic tetracarboxylic acid dianhydrides with substitution in the positions ortho to the bridging moiety and aromatic diamines, exhibiting solubility in organic solvents, increased glass transition temperatures, low coefficients of thermal expansion and photoimagability; said polyimides being suitable for the production of films, protective coatings and photolithographic relief images.

23 Claims, No Drawings

POLYIMIDES PREPARED FROM DISUBSTITUTED AROMATIC TETRACARBOXYLIC ACID DIANHYDRIDES

Polyimides find extensive use in electronic applications where they are useful in forming dielectric films on electrical and electronic devices such as capacitors and semiconductors. Typical uses for polyimides include protective coatings for semiconductors, dielectric layers for multilayer integrated circuits, high temperature solder masks, bonding multilayer circuits, final passivating coatings on electrical electronic devices and the like.

It is well known in the polymer art to make thermally stable all-aromatic polyimides by the condensation polymerization of dianhydrides and diamines to form polyamic acid. Such polyimide precursors are disclosed inter alia in U.S. Pat. No. 3,179,634. These polyamic acids are readily dehydrated to the corresponding polyimides by heating at high temperatures, e.g. 300° to 400° C. However, these earliest all-aromatic polyimides were insoluble and, therefore, protective films could not be coated in the polyimide form. Therefore, it has been prior practice to use instead the precursor polyamic acids which had the advantage of being readily soluble in many aprotic solvents. Such polyamic acid solutions were then coated to form the appropriate film and converted to the corresponding polyimide by heating the film at high temperature to effect volatilization of the solvent and dehydration of the polyamic acid to form the polyimide. However, polyamic acid solutions tend to have substantial viscosity instability which causes them to become lower in viscosity upon storage at room temperature. Therefore, it would be advantageous to have an already formed soluble polyimide which is viscosity stable and, because it requires no conversion, can be processed at relatively low temperatures, e.g. below 200° C.

A variety of approaches have been adopted for overcoming these deficiencies. For example, U.S. Pat. No. 3,856,752 discloses a fully imidized, soluble polyimide which incorporates a diamine monomer, diaminophenylindane, into the backbone strucure. Approaches which rely on diverse substitution patterns on the aromatic diamine components have also been disclosed. Corresponding approaches directed to modifying the tetracarboxylic acid function have been described in the literature. Such approaches have been exemplified in U.S. Pat. No. 4,629,777 and U.S. Pat. No. 4,698,295. Various aliphatic dianhydrides have been identified as conferring solubility on polyimides. For example, polyimides of alkylene diamines and 4,4'-(hexafluoroisoprupylidene)-bis(O-phthalic anhydride) are described in U.S. Pat. No. 4,631,335.

In preparing these polyimides, a broad range of tetracarboxylic acids and acid derivatives thereof have been identified for use. Listings of such materials appear in each of the above noted patents, with preference being indicated for the benzophenone types, i.e. benzophenone tetracarboxylic acid functionalities.

With the development of electronics and semiconductor technology, stringent requirements are imposed on the polyimides and the components utilized in the preparation thereof. The aforementioned solubility characteristics are only one of said requirements. Heat stability, high glass transition temperatures, ready cyclization, photocrosslinkability with increased photospeeds, photoimagability, and the like, are other desired properties. Although the polyimide systems available to date provide these performance characteristics to varying degrees, room for improvement particularly in terms of a broad spectrum of properties and applications still exists. Furthermore, existing polyimides when utilized in coating and laminating applications tend to exhibit undesirably high coefficients of thermal expansion. As a result, thermal stresses manifested in a number of ways are encountered.

Accordingly, it is a primary object of the invention to provide a class of polyimides based on select tetracarboxylic acid dianhydrides which impart a broad range of improved properties, including solubility, to said polyimides.

It is a further object to prepare such polyimides which exhibit a broad spectrum of improved properties to facilitate their use in a variety of applications.

It is another object to prepare formulated polyimide systems which can function as either positive or negative acting photosensitive systems.

Other objects and advantages of this invention will be evident from the following descriptions thereof.

It has now been surprisingly discovered that by utilizing aromatic tetracarboxylic acid dianhydrides containing substituents in each ortho position relative to the bridging moiety in the preparation of polyimides, a variety of benefits are imparted to the polyimides. Thus, such polyimides exhibit solubility in a wide variety of solvents, good thermal stability, higher glass transition temperatures, reduced coefficients of thermal expansion, increased photospeed of the crosslinking reaction in negative photoresist systems and solubility advantages regarding the developers used in positive photoresist systems. Such benefits are obtained in contrast to the preparation of polyimides utilizing unsubstituted dianhydride compounds (see U.S. Pat. No. 4,578,166).

The substituted dianhydrides utilized in the preparation of the polyimides of the instant invention correspond to the formula

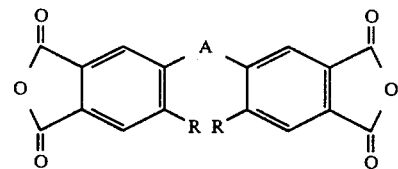

wherein A is a direct bond,

—O—, —S—, —SO—, —SO$_2$—, C$_1$-C$_3$alkylene, $$-\overset{O}{\underset{\|}{C}}-,$$

$$-\overset{CF_3}{\underset{CF_3}{\underset{|}{C}}}-, \quad -CF_2-CF_2- \text{ or } -CHOH-;$$

and R is independently halogen, C$_1$-C$_6$alkyl, OH, OR$_1$, NO$_2$, COOR$_1$, CF$_3$, (CF$_2$)$_{1-4}$CF$_3$, CN, SH or SOR$_1$, with R$_1$ being C$_{1-6}$alkyl. A is preferably a direct bond,

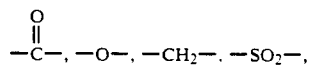

and most preferably

R is preferably halogen, methyl, ethyl, methoxy and most preferably chlorine.

By way of illustration, the preferred dichloro benzophenone dianhydride is generally prepared by reacting the appropriate starting aromatic compound with oxalyl chloride in the presence of aluminum chloride to prepare the 2,2'-dichloro-4,4',5,5'-tetramethylbenzophenone. The resulting compound is then oxidized, preferably in the presence of nitric acid, to form the tetracarboxylic acid intermediate. Finally, the acid is dehydrated in aromatic solvents and at elevated temperatures or at elevated temperature alone ranging from 180° to 290° C. or by recrystallization from dehydrating agents such as acetic anhydride to produce the dianhydride product. Other dianhydrides can be prepared by corresponding processes known in the art.

More details regarding the preparation of specific anhydrides are disclosed in U.S. Pat. No. 4,698,295, these preparative procedures being incorporated herein.

It is to be noted that 2,2'-dichloro-4,4',5,5'-benzophenone-tetracarboxylic dianhydride is preferred for purposes of this invention. Other applicable compounds are the corresponding diphenyl, diphenyl ether, diphenyl thioether, sulfoxide and sulfone compounds.

The polyimides of the invention are homo- and copolyimides of at least one of the aforementioned dianhydrides and at least one aromatic diamine which contain 5 to 100 mole % of at least one structural element of the formula (I)

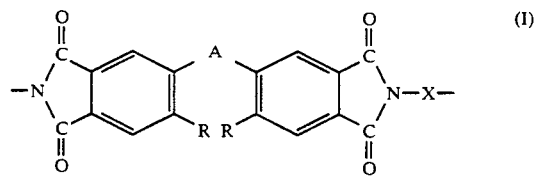

and 95 to 0 mole % of at least one structural element of the formula (II)

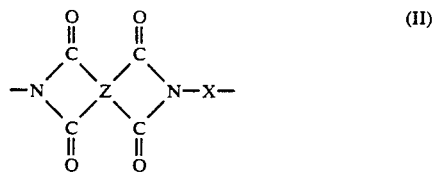

wherein A and R are as previously defined, Z is an unsubstituted or substituted tetravalent aromatic radical and X is an unsubstituted or substituted divalent radical of an aromatic diamine.

It is preferred that 20-100 mol % of elements of formula (I) be present and most preferred that 60-100 mol % of elements of formula (II) be present.

Examples of aromatic diamine radicals X are arylene radicals having 6 to 22 C atoms. These radicals can be mononuclear or represent polynuclear aromatic systems which are fused or mutually linked via bridge groups. Preferably they are phenylene radicals, such as 1,3- or 1,4- phenylene, or 1,3- or 1,4-phenylene radicals which are linked via a direct bond or a bridge group.

Particularly preferred homo- and copolyimides are those with structural elements of the formula I in which X is substituted aromatic radicals. The substituent on the aromatic radical preferably contains 1 to 20, in particular 1-12 and especially 1-6, C atoms. The substituent is, in particular, cycloalkyl with 5 or 6 ring carbon atoms, linear or branched alkyl, alkoxy, alkylthio, hydroxyalkyl, hydroxyalkoxy or hydroxyalkylthio with 1 to 12, in particular 1-6, C atoms, akoxyalkyl, alkylthioalkyl with 2 to 12, in particular 2-6, C atoms, benzyl, trimethylene or tetramethylene. Preferred alkoxyalkyl is alkoxymethyl and preferred alkoxy is methoxy. Examples of the substituents are: methyl, ethyl, propyl, isopropyl, n-butyl, isobutyl, pentyl, hexyl, octyl, dodecyl, tetradecyl, eicosyl, methoxy, ethoxy, propoxy, butoxy, pentoxy, hexoxy, methoxymethyl, methoxyethyl, ethoxymethyl, propoxymethyl, butoxymethyl, benzyl, methylbenzyl, phenylethyl, methylthio, ethylthio, hydroxyethyl, methylthioethyl and hydroxyethylthio. Preferred radicals are methoxymethyl, ethoxymethyl, methyl, ethyl, n-propyl, i-propyl, trimethylene and tetramethylene, cyclopentyl and cyclohexyl. Especially preferred radicals are, in particular, methyl, and ethyl and i-propyl. The substituted aromatic radical can be a mononuclear or polynuclear, in particular dinuclear, radical, in particular a mono- or dinuclear phenylene radical. Mononuclear radicals can contain up to 4, preferably 2, substituents and dinuclear radicals can contain up to 4, preferably 1 or 2, substituents in each nucleus. It has been found that the photosensitivity of those homo- or copolyimides in which one or two substituents are bonded in the ortho-position relative to the N atom is particularly high. Substitution in the ortho-position is therefore preferred. The aromatic radical is preferably bonded in the meta- or para-position relative to the N atom. In a preferred sub-group, the substituent of the aromatic radical contains 1 to 20 C atoms as alkyl or alkoxy, 2 to 12 C atoms as alkoxyalkyl, 5 or 6 ring atoms as cycloalkyl, 3 or 4 C atoms as alkylene and benzyl as aralkyl. The substituent is preferably alkyl with 1 to 4 C atoms, in particular isopropyl, ethyl and, especially, methyl.

A substituted aromatic radical X can contain 7 to 30, in particular 8 to 25, C atoms. The aromatic radical is preferably a pyridine radical, and in particular a hydrocarbon radical which is substituted by alkyl, alkoxyalkyl, alkoxy, trimethylene or tetramethylene. The aromatic radical can contain further substituents, for example, halide, such as Cl or Br. In a preferred sub-group, the aromatic radicals are phenylene radicals as mononuclear radicals, and naphthylene or bisphenylene as dinuclear radicals.

A preferred sub-group of polyimides according to the invention are those in which an aromatic radical X has the formulae III, IIIa and/or IIIb

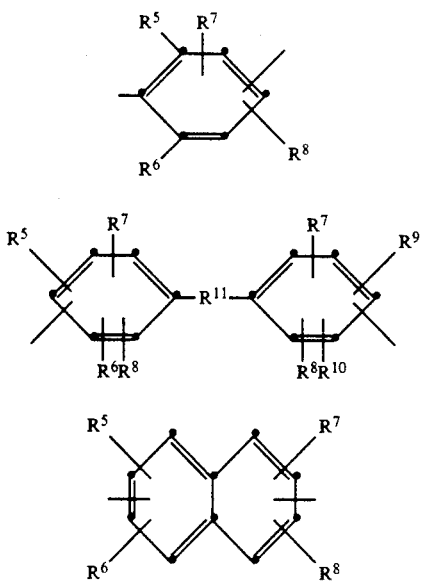 (III)

(IIIa)

(IIIb)

in which, in formula III, the free bonds are in the meta- or para-position relative to one another, in formula IIIa the free bonds are preferably in the meta- or para-position relative to the $R^{11}$ group and $R^5$ and $R^6$ are bonded in the two ortho-positions of the free bond, and in formula IIIb the free bonds are in the 2-, 3-, 6-, or 7-positions and $R^5$ and $R^6$ are in the two ortho-positions of the free bonds, $R^{11}$ is a direct bond, —O—, —S—, —SS—, —SO—, —SO$_2$—, —CO—, —COO—, —NH—,

with 1 to 6 C atoms in the alkyl,

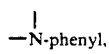

—N-benzyl, —CONH—, —CON-alkyl- with 1 to 6 C atoms in the alkyl, —CON-phenyl-, —CON-benzyl-,

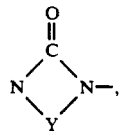

in which Y is

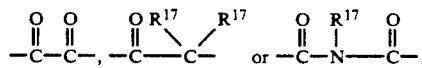

and $R^{17}$ is a hydrogen atom, $C_1$-$C_6$-alkyl or phenyl, linear or branched alkylene with 1 to 3 C atoms, alkylidene which has 2 to 12 C atoms and is unsubstituted or substituted by Cl or F, cycloalkylidene with 5 or 6 ring carbon atoms, phenylene, phenylenedioxy or the group $R^3SiR^4$,

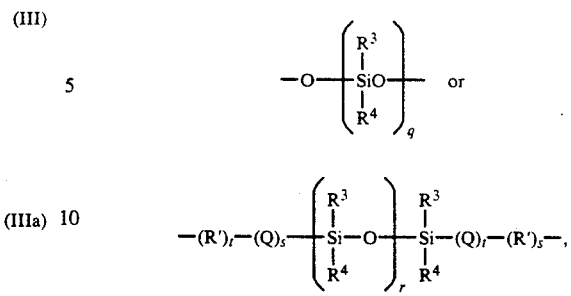

in which $R^3$ and $R^4$ are alkyl or alkoxy with 1 to 6 C atoms, phenyl, benzyl, phenoxy or benzyloxy, r is a number from 1 to 10, t is 0 or 1, s is 0 or 1, $R^1$ is —O— or —S—, Q is $C_1$-$C_6$-alkylene and q is a number from 1 to 100, $R^5$ and $R^6$ are alkyl, or alkoxy with 1 to 12 C atoms, alkoxyalkyl with 2 to 12 C atoms, cyclopentyl, cyclohexyl or benzyl, or, in the formula III or IIIa, $R^5$ and $R^7$ are bonded in adjacent positions and together are trimethylene or tetramethylene, in which case $R^6$ can also be a hydrogen atom, or $R^7$ and $R^8$ are hydrogen atoms or independently have the meanings of $R^5$ and $R^6$, and $R^9$ and $R^{10}$ are hydrogen atoms or independently have the meanings of $R^5$ and $R^6$, or $R^7$ and $R^9$ in formula IIIa together are trimethylene or tetramethylene. $R^5$ and $R^6$ are preferably alkyl with 1 to 6 C atoms, in particular methyl, ethyl, n-propyl or isopropyl. The free bonds of the formula IIIa are preferably in the meta-position or, in particular, para-position relative to the $R^{11}$ group. The alkyl in the $R^{11}$ radicals can be, for example, methyl, ethyl, propyl, isopropyl, n-butyl or pentyl. An alkylene radical $R^{11}$ is preferably ethylene or, in particular, methylene. An alkylidene radical $R^{11}$ preferably contains 2 to 6 C atoms. Examples are ethylidene, 2,2-butylidene, 2,2- or 3,3-pentylidene, hexafluoropropylidene and, in particular, 2,2-propylidene. A cycloalkylidene radical $R^{11}$ can be, for example, cyclopentylidene or, in particular, cyclohexylidene. The $R^{11}$ group is preferably a direct bond, —O—, —S—, —SO$_2$—, —CO—, alkylene or alkylidene. $R^{11}$ is particularly preferably a direct bond, —O—or, in particular, —CO— or —CH$_2$—. $R^3$ and $R^4$ are preferably alkyl, in particular methyl or phenyl. R is preferably —O—, Q is preferably methylene or ethylene, q is preferably a number from 1 to 10 and r is a number from 1 to 20, in particular 1 to 10.

Another group of diamine radicals are those of the formula

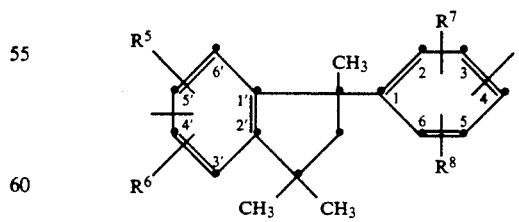

in which $R^5$, $R^6$, $R^7$ and $R^8$ are hydrogen or one free bond is in the 4'- or 5'-position and the other is in the 3-, or 5- or, preferably, 4-position and $R^5$ and $R^6$ and/or $R^7$ and $R^8$ are in the ortho-positions of the free bond and are alkyl or alkoxy with 1 to 12 C atoms or alkoxyalkyl with 2 to 12 C atoms.

A particularly preferred sub-group of polyimides according to the invention are those in which X in formula I is a radical of the formula

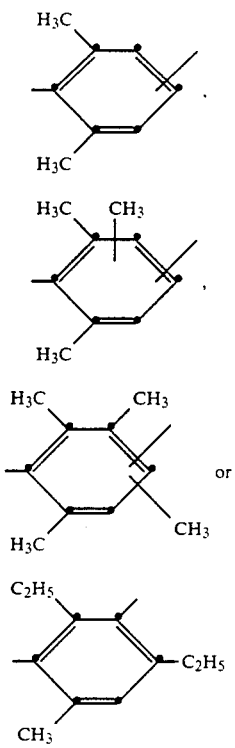

in which the free bonds are in the meta- or para-position relative to one another, or of the formula

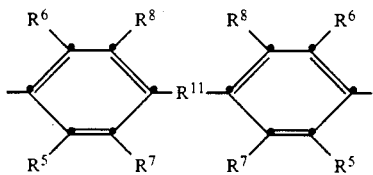

in which $R^5$ and $R^6$ independently of one another are methyl, ethyl, n-propyl or isopropyl, $R^7$ and $R^8$ are hydrogen atoms or have the meaning of $R^5$, or $R^5$ and $R^7$ together are trimethylene or tetramethylene and $R^6$ and $R^8$ are hydrogen atoms, and $R^{11}$ is a direct bond, $CH_2$, 2,2-propylidene or CO. Of these dinuclear radicals, those in which $R^5$, $R^6$, $R^7$ and $R^8$ are methyl are particularly preferred. Copolyimides which contain at least 2 different radicals of these formulae are a further preferred embodiment of the invention.

Copolyimides according to the invention contain at least two different structural elements, the number of different structural elements essentially depending on the desired properties and the field of use. They preferably contain 2 to 4 different structural elements, in which case the structural elements may differ only in the radical X in the formula I. In a particularly preferred embodiment of such copolyimides, the polymers contain structural elements of ortho-disubstituted phenylenes, in particular of 1,3-phenylenes.

Examples of X are: 2,6-dimethyl-1,4- or -1,3-phenylene, 2,6-diethyl-1,4- or -1,3-phenylene, 2,6-dimethyl-5-chloro-1,4- or -1,3-phenylene, 2-methyl-6-ethyl-1,4- or -1,3-phenylene, 2-methyl-6-isopropyl-1,4- or -1,3-phenylene, 2,6-diisopropyl-1,4- or -1,3-phenylene, 2,6-dimethoxy-1,4- or -1,3-phenylene, 2,6-diethoxy-1,4- or -1,3-phenylene, 2-methyl-6-methoxy-1,4- or -1,3-phenylene, 2,6-dibenzyl-1,4- or -1,3-phenylene, 2,6-dimethoxymethyl-1,4- or -1,3-phenylene, 2,5,6-trimethyl-1,4- or -1,3-phenylene, 2,5,6-triethyl-1,4- or -1,3-phenylene, 2,4,6-trimethyl-1,3-phenylene, 2,3,5,6-tetramethyl-1,4-phenylene, 2,4,5,6-tetramethyl-1,3-phenylene, tetrahydro-1,4- or -1,3-naphthylene and radicals of the formulae

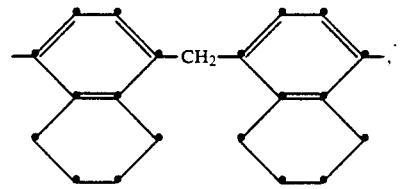

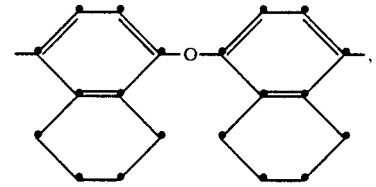

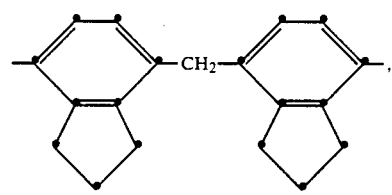

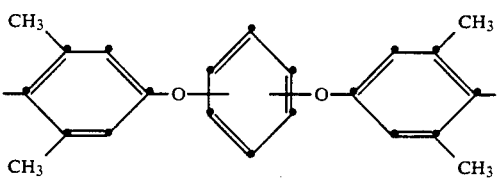

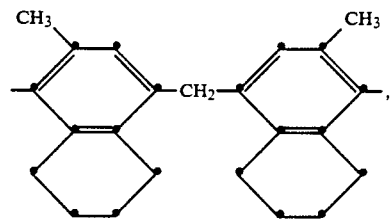

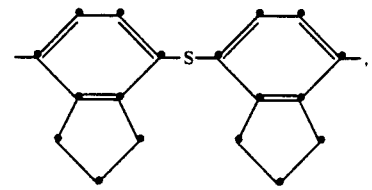

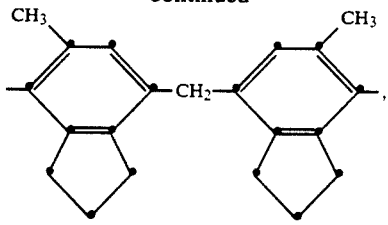

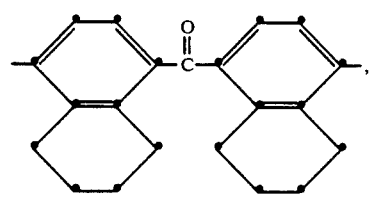

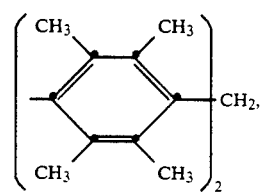

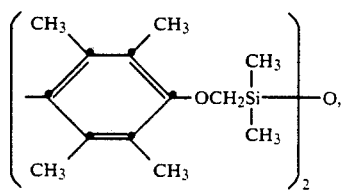

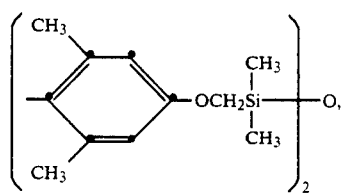

as well as

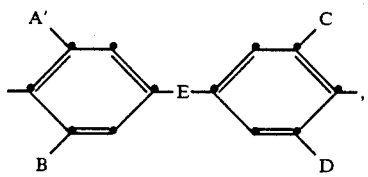

and

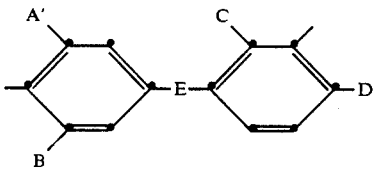

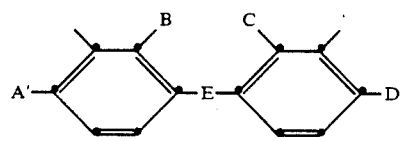

in which A', B, C, D and E have the meanings given in the table which follows. The free positions in the phenyl nuclei can be occupied by one or two other substituents G or H in each nucleus, it being possible for G or H to have the meaning given in the following table:

| E | A' | B | C | D |
|---|---|---|---|---|
| $CH_2$ | Methyl | Methyl | H | H |
| $CH_2$ | Methyl | Ethyl | H | H |
| $CH_2$ | Ethyl | Ethyl | H | H |
| $CH_2$ | Isopropyl | Isopropyl | H | H |
| $CH_2$ | | Methoxymethyl | H | H |
| $CH_2$ | Benzyl | Benzyl | H | H |
| $CH_2$ | Methyl | Methyl | Methyl | H |
| $CH_2$ | Ethyl | Ethyl | Ethyl | H |
| $CH_2$ | Isopropyl | Isopropyl | Methyl | Methyl |
| $CH_2$ | | Methoxymethyl | Methyl | H |
| $CH_2$ | Methyl | Ethyl | Methyl | H |
| $CH_2$ | | Methoxymethyl | | Methoxymethyl |
| $CH_2$ | Methyl | Methyl | Methyl | Methyl |
| $CH_2$ | Ethyl | Ethyl | Ethyl | Ethyl |
| $CH_2$ | Methyl | Methyl | Ethyl | Ethyl |
| $CH_2$ | Ethyl | Ethyl | Isopropyl | Isopropyl |
| $CH_2$ | Isopropyl | Isopropyl | Isopropyl | Isopropyl |
| $CH_2$ | Isopropyl | Isopropyl | Methyl | H |
| $CH_2$ | Methoxy | Methoxy | Methyl | Methyl |
| O | Methyl | Methyl | H | H |
| O | Ethyl | Ethyl | H | H |
| O | Methyl | Methyl | Methyl | H |
| O | Methyl | Methyl | Methyl | Methyl |
| O | Methyl | Methyl | Ethyl | Ethyl |
| S | Methyl | Methyl | H | H |
| S | Ethyl | Ethyl | H | H |
| S | Methyl | Methyl | H | H |
| S | Methyl | Methyl | Methyl | Methyl |
| S | Ethyl | Ethyl | Ethyl | Ethyl |
| S | Methyl | Methyl | Ethyl | Ethyl |
| CO | Methyl | Methyl | Methyl | H |
| CO | Methyl | Methyl | H | H |
| CO | Methyl | Methyl | Methyl | Methyl |

-continued

| E | A | B | C | D |
|---|---|---|---|---|
| SO₂ | Methyl | Methyl | Ethyl | H |
| SO₂ | Methyl | Methyl | Methyl | Methyl |
| SO₂ | Ethyl | Ethyl | Methyl | Methyl |
| SO | Methyl | Methyl | Methyl | Methyl |
| SO | Methyl | Methyl | H | H |
| COO | Methyl | Methyl | H | H |
| COO | Methyl | Methyl | Methyl | Methyl |
| CONCH₃ | Methyl | Methyl | H | H |
| NCH₃ | Methyl | Methyl | Ethyl | Ethyl |
| NCH₃ | Methyl | Methyl | Methyl | Methyl |
| CONH | Methyl | Methyl | — | — |
| NH | Ethyl | Methyl | Ethyl | Methyl |
| NH | Methyl | Methyl | Methyl | Methyl |
| Si(Methyl)₂ | Methyl | Methyl | H | H |
| Si(Phenyl)₂ | Methyl | Methyl | Methyl | Methyl |
| Si(OMethyl)₂ | Ethyl | Ethyl | H | H |
| Si(OPhenyl)₂ | Methyl | Methyl | Methyl | Methyl |
| —OSi(Methyl)₂O— | Methyl | Methyl | Methyl | Methyl |
| Ethylene | Methyl | Methyl | H | H |
| Ethylene | Methyl | Methyl | Methyl | Methyl |
| Ethylene | Ethyl | Ethyl | H | H |
| Ethylene | Methyl | Methyl | Ethyl | Ethyl |
| Phenylene | Methyl | Methyl | Methyl | Methyl |
| Phenylene | Ethyl | Ethyl | H | H |
| (CH₃)₂C< | Methyl | Ethyl | Methyl | Ethyl |
| (CH₃)₂C< | Methyl | Methyl | Methyl | Methyl |
| (CF₃)₂C< | Methyl | Methyl | Methyl | Methyl |
| direct bond | Methyl | Methyl | H | H |
| direct bond | Methyl | Ethyl | Methyl | Ethyl |
| direct bond | Methyl | Ethyl | Methyl | H |
| direct bond | Ethyl | Ethyl | Ethyl | Ethyl |
| direct bond | Methoxy | Methoxy | Methoxy | Methoxy |
| direct bond | Isopropyl | Isopropyl | H | H |
| direct bond | Methoxymethyl | Methoxymethyl | Methoxymethyl | Methoxymethyl |

In another preferred embodiment, a substituted aromatic radical X has the formula

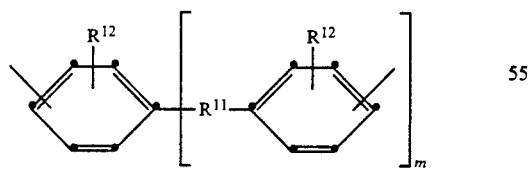

in which m is 0 or 1, the free bonds are in the meta- or, preferably, in the ortho-position relative to the $R^{12}$ group, $R^{11}$ is as defined for formula IIIa and $R^{12}$ has the same meaning as $R^5$. The free bonds are preferably in the para- or, in particular, meta-position relative to the $R^{11}$ group.

A preferred sub-group are arylene radicals of the formulae

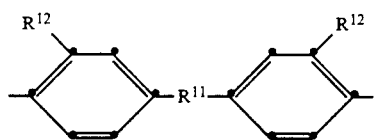

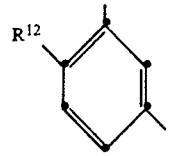

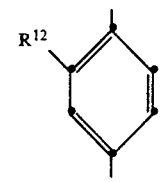

in which $R^{11}$ is a direct bond, —O—, —CO— or —CH$_2$— and $R^{12}$ is methyl, ethyl, isopropyl, methoxy, ethoxy, hydroxy, carboxy or a hydrogen atom.

Examples of diamines H$_2$N—X—NH$_2$ with an aromatic radical of one of these formula are: 4,4'-methylenebis(3-methylaniline), 4,4'-methylenebis-(2-ethylaniline), 4,4'-methylenebis-(2-methoxyaniline), 5,5'-methylenebis-(2-aminophenol), 4,4'-methylenebis-(2-methylaniline), 4,4'-oxybis-(2-methoxyaniline), 4,4'-thiobis-(2-methylaniline), 4,4'-thiobis-(2-methoxyaniline), 4,4'-sulfonylbis-(2-methylaniline), 4,4'-sulfonylbis-(2-ethoxyaniline), 3,3'-dimethyl-4,4'-diaminobenzophenone, 3,3'-dimethoxy-4,4'-diaminobenzophenone, 4,4'-methylenedianiline, 3,3'-dimethylbenzidine, 3,3'-dimethoxybenzidine, diaminotoluene and 5-amino-1-(4-aminophenyl)-1,3,3-trimethylindane.

A diamine radical X can be, for example, phenylene which is unsubstituted or substituted by halogen or C$_1$–C$_4$-acyl, or bisphenylene of the formula

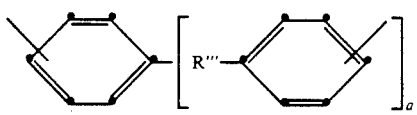

in which $a$ is 0 or 1 and R''' is a direct bond, —O—, —S—, —SS—, —SO—, —SO$_2$—, —CO—,

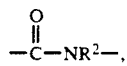

—COO—, —NR$^2$—, —NH—, —CONH—, —SiR$^3$R$^4$— or —OSi(R$^3$R$^4$)O—, and R$^2$, R$^3$ and R$^4$ are C$_1$–C$_6$-alkyl, phenyl or benzyl and R$^3$ and R$^4$ are also C$_1$–C$_6$-alkoxy, phenoxy or benzyloxy. The free bonds are preferably in the para-position or, in particular, in the meta-position relative to the R''' group. Examples of such diamines are: 3,3'-dichlorobenzidine, 3,3'-sulfonyldianiline, 4,4'- or 3,3'-diaminobenzophenone, 1,5-diaminonaphthalene, bis-(4- or 3-aminophenyl)-dimethylsilane, bis-(4- or 3-aminophenoxy)-dimethylsilane, N-bis(4-aminophenyl)N-methyl- or -N-phenylamine, 4,4'-oxybis(2-chloroaniline), 5,5'-oxybis(2-aminophenol), 4,4'-thiobis(aniline), 4,4'-sulfonylbis(2-chloroaniline), 5,5'-sulfonylbis(2-aminophenol), 3,3'-dichloro-4,4'-diaminobenzophenone, 4,4'- or 3,3'-diaminobisphenyl, m-phenylenediamine, p-phenylenediamine, 4,4'-oxydianiline, 4,4'- or 3,3'-thiodianiline, 4,4'-sulfonyldianiline and 3,3'-dicarboxybenzidine.

A divalent aromatic radical Z preferably contains 6 to 30, in particular 6 to 20, C atoms. In a preferred sub-group, Z has the formulae

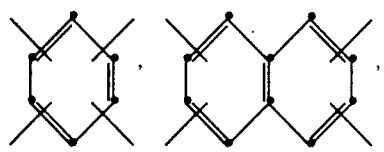

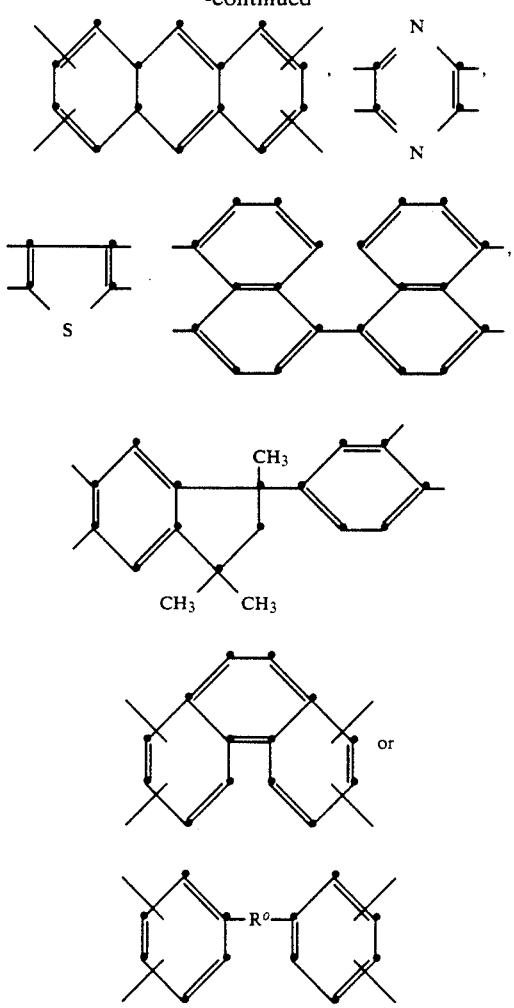

in which $R^o$ is a direct bond or a bridge group of the formula

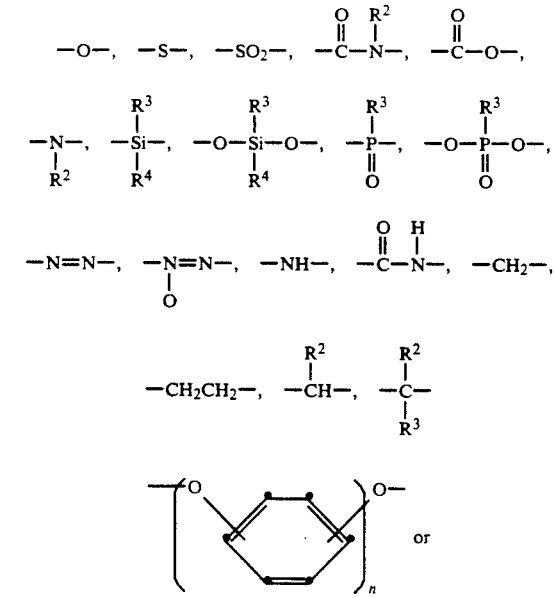

-continued

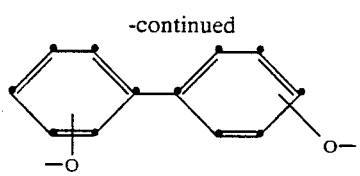

in which $R^2$, $R^3$ and $R^4$ are alkyl with 1 to 6 C atoms, phenyl or benzyl, and $R^3$ and $R^4$ are alkoxy with 1 to 6 C atoms, phenoxy or benzyloxy.

In the above formulae, in each case two of the free bonds are always in the peri- and/or ortho-position.

A preferred sub-group for Z are radicals of the formulae

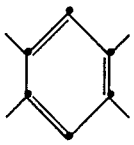

and/or

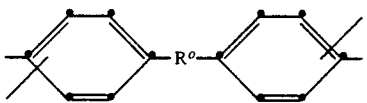

in which $R^o$ is a direct bond, —O—, —SO$_2$—, —CH$_2$— or, in particular, —CO—.

Radicals of the formulae

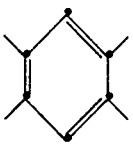

and/or

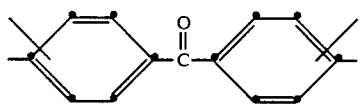

or mixtures thereof, for example those with at least 5 mol % of tetravalent benzophenone radicals, are very particularly preferred. The free bonds in the benzophenone radical are in the ortho-position.

Examples of tetracarboxylic acid anhydrides with a radical Z are: 2,3,9,10-perylenetetracarboxylic acid dianhydride, 1,4,5,8-naphthalenetetracarboxylic acid dianhydride, 2,6-dichloronaphthalene-1,4,5,8-tetracarboxylic acid dianhydride, 2,7-dichloronaphthalene-1,4,5,8-tetracarboxylic acid dianhydride, 2,3,6,7-tetrachloronaphthalene-1,4,5,8-tetracarboxylic acid dianhydride, phenanthrene-1,8,9,10-tetracarboxylic acid dianhydride, pyromellitic dianhydride, 3,3',4,4'-biphenyltetracarboxylic acid dianhydride, 2,2',3,3'-biphenyltetracarboxylic acid dianhydride, 4,4'-isopropylidenediphthalic anhydride, 3,3'-isopropylidenediphthalic anhydride, 4,4'-oxydiphthalic anhydride, 4,4'-sulfonyldiphthalic anhydride, 3,3'-oxydiphthalic anhydride, 4,4'-methylenediphthalic anhydride, 4,4'-thiodiphthalic anhydride, 4,4'-ethylidenediphthalic anhydride, 2,3,6,7-naphthalenetetracarboxylic acid dianhydride, 1,2,4,5-naphthalenetetracarboxylic acid dianhydride, 1,2,5,6-naphthalenetetracarboxylic acid dianhydride, benzene-1,2,3,4-tetracarboxylic acid dianhydride, thiophene-2,3,4,5-tetracarboxylic acid dianhydride, 1-(3',4'-dicarboxyphenyl)-1,3,3-trimethylindane-5,6-dicarboxylic acid dianhydride, 1-(3',4'-dicarboxyphenyl)-1,3,3-trimethylindane-6,7-dicarboxylic acid dianhydride, 1-(3',4'-dicarboxyphenyl)-3-methylindane-5,6-dicarboxylic acid dianhydride, 1-(3',4'-dicarboxyphenyl)-3-methylindane-6,7-dicarboxylic acid dianhydride, 3,3',4,4'-benzophenonetetracarboxylic acid anhydride and 4,5,3',4'-benzophenonetetracarboxylic acid anhydride.

The polyimides according to the invention have average molecular weights (weight-average $\overline{M}w$) of at least 2,000, preferably at least 5,000. The upper limit essentially depends on properties which determine the processability, for example the solubility of the polyimides. It can be up to 500,000, preferably up to 100,000 and in particular up to 60,000. The polymers can furthermore be random polyimides or block polyimides.

Of particular interest are polyimides prepared from 2,2'-dichloro-4,4',5,5'-benzophenonetetracarboxylic acid dianhydride and 3,5-diaminobenzoic acid in view of solubility in organic solvents and aqueous alkali (positive photoresists) when fully cyclized, high glass transition temperature and low coefficient of thermal expansion, which will be explored in greater detail.

The preparation of the polyimides is advantageously carried out in solution, suitable inert solvents are listed below. The reaction temperatures can be −20° to 300° C. The dianhydride and diamine are reacted in approximately equimolar amounts ±3%. In detail, a procedure is advantageously followed in which the tetracarboxylic dianhydride and diamine are first reacted to form a polyamic acid precursor and this polyamic acid is then cyclized, water being detached. Cyclization can be carried out under the influence of heat. The cyclization is advantageously carried out under the influence of dehydrating agents, for example carboxylic anhydrides, such as acetic anhydride. The polyimides can then be isolated by customary processes, for example by removal of the solvent or precipitation by addition of a non-solvent.

Another preparation method comprises reacting the tetracarboxylic dianhydride with a diisocyanate in one stage to give the polyimide.

The polyimides according to the invention are soluble in various solvents, if necessary with warming, and they have high glass transition points. They are outstandingly suitable for the production of films and protective coatings, and coating agents from a solution of the polyimide in a solvent can be used. The present invention also relates to the use of the polyimides according to the invention for the production of protective coatings and films.

To prepare the coated material, the polymer or a mixture thereof is advantageously dissolved in a suitable organic solvent, if necessary with warming. Suitable solvents are, for example, polar aprotic solvents, which can be used by themselves or as mixtures of at least two solvents. Examples are: ethers, such as dibutyl ether, tetrahydrofuran, dioxane, methylene glycol, dimethylethylene glycol, dimethyldiethylene glycol, diethyldiethylene glycol and dimethyltriethylene glycol, halogenated hydrocarbons, such as methylene chloride, chloroform, 1,2-dichloroethane, 1,1,1-trichloroethane and 1,1,2,2,-tetrachloroethane, carboxylic acid esters and lactones, such as ethyl acetate, methyl propionate, ethyl benzoate, 2-methoxyethyl acetate, γ-butyrolactone, o-valerolactene and pivalolactone, carboxylic acid amides and lactams, such as formamide, acetamide, N-methylformamide, N,N-dimethylformamide, N,N-diethylformamide, N,N-dimethylacetamide, N,N-diethylacetamide, γ-butyrolactam, ε-caprolactam, N-methylpyrrolindone, N-acetylpyrrolidone, N-methylcaprolactam, tetramethylurea and hexamethylphosphoric acid triamide, sulfoxides, such as dimethyl sulfoxide, sulfones, such as dimethyl sulfone, diethyl sulfone, trimethylene sulfone and tetramethylene sulfone, amines, such as trimethylamine, triethylamine, N-methylpiperidine and N-methylmorpholine, and substituted benzenes, such as chlorobenzene, nitrobenzene, phenols or cresols.

Undissolved constituents can be removed by filtration, preferably pressure filtration. The concentration of polymer in coating agents thus obtained is preferably not more than 50% by weight, in particular not more than 30% by weight and especially not more than 20% by weight, based on the solution.

Other customary additives which do not adversely influence the photosensitivity can be incorporated during preparation of the solution. Examples of these are matting agents, flow control agents, finely divided fillers, flameproofing agents, fluorescent brighteners, antioxidants, light stabilisers, stabilisers, dyes, pigments, adhesion promoters and antihalo dyes, such as are described, for example, in U.S. Pat. No. 4,349,619.

The coating agent can be applied to suitable substrates or carrier materials by means of customary methods, such as immersion, brushing and spraying processes, or whirler, cascade and curtain coating, and adhesion promoters or adhesive layers can also be used. Suitable substrates are, for example, plastics, metals and metal alloys, semimetals, semiconductors, glass, ceramics and other inorganic materials, for example $SiO_2$ and $Si_3N_4$. The solvent is then removed, if necessary by warming and if necessary in vacuo. Tack-free, dry and uniform films are obtained. Depending on the use, the films applied can have coating thicknesses of up to about 500 μm or more, preferably from 0.5 to 500 μm and in particular from 1 to 50 μm.

It has been found that the polyimides according to the invention are autophotocrosslinkable and can be crosslinked under the influence of radiation to produce negative photoresists, i.e. the irradiated areas of the layer remain as a relief structure after the non-exposed areas are dissolved away by a development process, when the bridging group in at least one dianhydride is carboxy and the diamine is substituted in the ortho- position relative to at least one nitrogen atom.

Protective films of such polyimides can be further modified by the influence of radiation, so that, for example, increased heat stabilities are possible. There is also the possibility of employing such polyimides as photographic recording material for relief images. As a result of direct crosslinking under the influence of radiation, additives such as sensitisers can be avoided and the protective coatings and images have excellent electrical properties. The protective coatings and images are furthermore distinguished by their high heat stability and by only little or no shrinkage when exposed to heat, which has considerable advantages during use, because virtually no distortion of imaged structures is observed.

The invention also relates to coating agents containing such a radiation-sensitive polyimide in solution, a carrier material coated with such polyimides and the use of this material for the production of protective coatings and photographic relief images. The coating thickness for this use is preferably 0.5 to 100 μm, in particular 1 to 50 μm and especially 1–10 μm.

Photostructuring or photocrosslinking can be caused by high-energy radiation, for example by light, in particular in the UV range, or by X-rays, laser light, electron beams and the like. The material according to the invention is outstandingly suitable for the production of protective films and passivating lacquers and as photographic recording material for heat-stable relief images.

Fields of use are, for example, protective, insulating and passivating varnishes in electrical engineering and electronics, photomasks for electronics, textile printing and the graphics industry, etch resists for the production of printed circuits and printed circuit boards and integrated circuits, relays for the production of X-ray masks, solder-stopping varnishes, dielectrics for multilayer circuits and structural elements for liquid crystal display units.

Protective films are produced by direct exposure to light, the exposure times essentially depending on the coating thicknesses and the photosensitivity.

Photographic production of the relief structure is effected by image-wise exposure to light through a photomask and subsequent development, removing the non-exposed portions, with a solvent or a solvent mixture, after which, if appropriate, the image produced can be stabilised by after-treatment with heat.

The invention also relates to such a process for the application of relief structures. Suitable developers are, for example, the abovementioned solvents.

The polymer layer of the material according to the invention has a photosensitivity which is sufficient for many application purposes and is in some cases high, and it can be photocrosslinked directly. The protective films and relief images are distinguished by a high adhesive strength and resistance to heat, mechanical stresses and chemicals. Only slight shrinkage is observed during after-treatment with heat. Additives to produce or increase photosensitivity can furthermore by avoided. The material is stable on storage, but is advantageously to be protected from the influence of light.

By way of specific advantages of the polyimides of the invention, a number can be identified in addition to the solubility, stability and fully cyclized features. Relative to the photospeed of the crosslinking reaction in negative photoresists, the inclusion of the instant dianhydrides provide desirable increases ranging up to about 250% depending on the specific conditions utilized and relative to conventional substitution patterns. Such increases allow for reduced energy usage for insolubilization together with an increase in the number of coated substrates produced per unit of time. Correspondingly, the aforementioned physical properties of the polymer are improved by the inclusion of the instant dianhydrides. Polyimide systems of dichlorobenzophenonetetracarboxylic acid dianhydride, 4,4'-diamino-3,3'-diethyl-5,5'-dimethyl-diphenyl methane, durene diamine, diethyltoluene diamine and diamino mesitylene are representative of such polymers with increased photospeed.

As previously noted, the instant soluble polyimides exhibit lower coefficients of thermal expansion. Such low values are beneficial inasmuch as they enable the coefficient of the polymer coating to approach that of the substrate, thereby reducing undesirable stresses in the coating.

Regarding the positive photoresist systems of the invention, these are based on polyimides prepared from the aforementioned dianhydrides and at least 30 mol % aromatic diamines containing acidic or phenolic functionalities. Representative diamines include 3,5-diaminobenzoic acid, 3,3'-dicarboxybenzidine, diaminophenols, 3,3'-dihydroxy-4,4 '-diaminobiphenyl, (bis-aminocarboxyphenyl)methane, (bis-aminodihyroxyphenyl) methane, (bis-aminophenylsulfonic acid) methane, diaminophenyl sulfonic acid, and the like. In addition, it is essential that dissolution inhibitors are included with the polyimide systems in order to allow for the required dissolution of the exposed areas. Typical dissolution inhibitors are known to those skilled in the art. Most prominent are diazonaphthoquinones such as THBP-214 Diazo Ester type 3.3, THBP-214 Diazo Ester type 3.5 and Diazo Sensitizer type 1.55 from ICI Americas. These materials are generally partially esterified trihydroxybenzophenones connected via $SO_2$ groups to naphthalene diazo compounds. The inhibitors are generally utilized in concentrations ranging from 10–35%, and preferably 10–25%, by weight of polyimide. The coating and irradiation procedures are as previously noted for the negative acting systems. Subsequent to photoimaging, the exposed areas are available for development by the application of basic aqueous developers such as tetramethylammoniumhydroxide, buffered sodium hydroxide and dibasic sodium phosphate (respectively, SB-312, 351 and DE3 from KTI Chemicals). Such developers which eliminate the need for organic solvents are most desirable in terms of environmental and toxicological issues. Additionally, these positive acting systems of the instant invention exhibit good thermal properties and can be utilized in higher temperature processes than standard novolac resin-based systems.

The following examples will further illustrate the embodiments of the instant invention. In these examples, all parts given are by weight unless specifically indicated otherwise.

EXAMPLE 1

Synthesis of 2,2'-dichloro-4,4',5,5'-benzophenonetetracarboxylic dianhydride

A flask fitted with mechanical stirrer, nitrogen inlet, thermometer, condenser and caustic filled HCl traps is charged with 4-chloro-o-xylene (560 g, 3.98 moles) and oxalyl chloride (272 g, 2.14 moles) which is washed with 2000 mls of $CS_2$. The reaction mixture is then cooled to 0° C. and aluminum chloride (584 g, 4.38 moles) is then added in eight equal portions over a 2 hour period. The reaction is warmed to room temperature and stirred for an additional 20 hours. The reaction mixture is then diluted with 800 mls of $CHCl_3$ and poured over ice with stirring whereupon the aluminum complex is filtered off. The organic layer is removed and the aqueous layer is then extracted with 4×400 mls of $CHCl_3$. The combined organic phase is then washed with 3×500 mls $H_2O$ and 500 mls of a saturated NaCl solution. The organic layer is dried over $MgSO_4$ and then concentrated under reduced pressure. The crude 2,2'-dichloro-4,4',5,5'-tetramethylbenzophenone is recrystallized from isopropyl ether in a ratio of 100 g crude product to 2250 mls of isopropyl ether. The yield is 459 g (75%); m.p. 148°–9° C.

Analysis: C: 66.46%, H: 5.25%, O: 5.21%, Cl: 23.08%;

Found: C: 66.8%, H: 5.5%, O: 5.2%, Cl: 23.1%.

The 2,2'-dichloro-4,4',5,5'-tetramethylbenzophenone (20.4 g, 66.4 mmoles) is charged to a glass pressure flask and rinsed in with 500 mls of 20% $HNO_3$. The flask is sealed with an all glass pressure relief valve and then placed in a titanium pressure reactor with 400 mls of water surrounding the flask. The reactor is then sealed and heated at 180° C. for 24 hours. The glass pressure flask is removed and cooled in an ice bath to precipitate the 2,2'-dichloro-4,4',5,5'-benzophenonetetracarboxylic acid product. The product is filtered and the residual $HNO_3$ is then removed by washing the solid with ice water. The yield is 17.3 g (85%).

Analysis: C: 47.80%, H: 1.89%, O: 33.71%, Cl: 16.60%;

Found: C: 48.19%, H: 2.12%, O: 33.45%, Cl: 16.14%.

A 2000 ml 3-neck flask fitted with mechanical stirrer, $N_2$ inlet, condenser, and Dean-Stark trap is charged with the 2,2'-dichloro-4,4',5,5'-benzophenonetetracarboxylic acid (222 g, 0.519 moles) and 1330 mls of a solvent composed of 73.5% phenyl ether and 26.5% biphenyl. The reaction mixture is heated to 230° C. and maintained for 8 hours under $N_2$. A dark brown solution results. Upon cooling to room temperature, the 2,2'-dichloro-4,4',5,5'-benzophenonetetracarboxylic dianhydride product is precipitated. The product is filtered, washed with $CHCl_3$ and then recrystallized from acetic anhydride (1500 mls). The yield is 183 g (90%). $^{13}C$-NMR 191.0 δ (C=O), 162.1 δ, 162.3 δ (anh.C=O), 140.0 δ (C—Cl).

EXAMPLE 2

Synthesis of polyimides.

A 500 ml 3-neck flask fitted with mechanical stirrer and $N_2$ inlet is charged with the indicated diamine (approximately 75 mmoles) and with approximately 100 mls of N-methyl pyrrolidone (NMP). After the diamine dissolves, the reaction mixture is cooled to approximately 0° C. in an ice bath. One equivalent of the dianhydride of Example 1 is added with enough NMP to bring the final reaction mixture to about 20% solids. After the initial heat of reaction subsides, the ice bath is removed and the reaction is stirred for 16 hours at room temperature to form a polyamic acid. The reaction mixture is then diluted to 10% solids with NMP and cyclized chemically with the addition of acetic anhydride (150 mmoles) and pyridine (75 mmoles). During this cyclization step, the polymers remain in solution. The resulting, soluble polyimide is then isolated by precipitating the reaction mixture into a 10 fold volume excess of 18 ΩM water with sheer. The polymer is washed repeatedly with 18 ΩM water and dried under reduced pressure overnight at 110° C.

EXAMPLE 3

The performance characteristics of the various polyimides prepared according to the procedure of Example 2 are determined according to the following procedures.

Solubility—Samples stirred in NMP at 40° C. for 16 hours or until earlier solubility at 5% solids concentration is observed.

Inherent Viscosity—Measured as a 0.5%, by weight, solution in NMP at 25° C. utilizing a Cannon-Ulbelhode dilution viscometer.

Glass Transition Temperature—Measured utilizing Perkin Elmer Differential Scanning Calorimeter with heating to 400° C. at 10° C./min.

Thermal Stability—Measured as (a) 5% decomposition weight loss after preheating to 240° C. for 10 minutes, cooling to 100° C. and heating to 600° C. at 10° C./minute until 5% weight loss; and (b) weight loss after preheating to 340° C. for 10 minutes, and heating at 350° C. for 1 hour.

Solubility comparisons are also conducted with comparable polyimides prepared utilizing 3,3′,4,4′-benzophenonetetracarboxylic dianhydride (BTDA).

The results are noted in Tables 1 and 2.

TABLE 1

| DIAMINE MONOMER | SOLUBILITY BTDA | SOLUBILITY DCBTDA |
|---|---|---|
| DAPI | + | + |
| DAM | + | + |
| MPDA | − | (+)[1] |
| BDB | − | + |
| DABA | − | + |
| MDB | − | + |
| DBF | − | + |
| CMDA | − | + |
| DCPDA | − | +[2] |

[1] Soluble but crystallizes out upon standing at room temperature.
[2] Soluble but difficult to dissolve completely.
DAPI = diaminophenylindane
MPDA = 1,3-phenylene diamime
DABA = 3,5-diaminobenzoic acid
DBF = 3,5-diaminobenzotrifluoride
DAM = diaminomesitylene
BDB = 5-t-butyl-1,3-phenylene diamine
MDB = 3,5-diaminomethylbenzoate
CMDA = 5-chloro-1,3-phenylene diamine
DCPDA = 2,5-dichloro-1,4-phenylene diamine

TABLE 2

| Diamine Monomer | Viscosity (inh, dl/g) | T$_g$ (°C.) by DSC | Decomposition 5% wt. loss (°C.) | Stability-wt loss (%) 1 Hr. @ 350° C. |
|---|---|---|---|---|
| DAPI | 0.50 | 333 | 488 | 0.35 |
| DAM | 0.47 | 371* | 506 | 0.36 |
| MPDA | 0.48 | 313 | 551 | 0.44 |
| BDB | 0.11 | 290 | 464 | 0.53 |
| DABA | 0.43 | 368 | 403 | 1.63 |
| MDB | 0.58 | 321 | 464 | 0.68 |
| DBF | 0.33 | 305 | 567 | 0.37 |
| CMDA | 0.39 | 311 | 563 | 0.35 |
| DCPDA | — | 367* | 498 | 0.77 |

*No clear T$_g$ observed. Temperature reported is onset of exotherm.

These data thus clearly indicate the beneficial characteristics of the polyimides of the instant invention when utilizing the dichloro dianhydride component.

EXAMPLE 4

6.08 grams of 3,5-diaminobenzoic acid (0.04 moles) is dissolved under N$_2$ in 60 mls of fresh NMP in a 300 ml 3-neck flask fitted with mechanical stirrer. 15.65 grams of DCBTDA (0.04 moles) is added and rinsed in with 24 mls of NMP to bring the final reaction mixture to 20% solids. Stirring is continued for 18 hours.

The polyamic acid solution is diluted to 10% solids and cyclized to the polyimide by adding 3.8 mls of pyridine and then 7.6 mls of acetic anhydride (0.08 moles). This is stirred overnight. The polyimide is precipitated into acidic (HCl) water in a blender. After filtration, the polymer is suction dried in air, reground in an excess of fresh slightly acidic water and filtered.

The polyimide is dried at 140° C. under house vacuum overnight. 20.3 grams (100%) of a pale yellow colored solid polyimide is obtained. The inherent viscosity of a 0.5% solution in NMP at 25° C. is 0.43 dl/g.

EXAMPLE 5

The procedure of Example 2 is repeated utilizing the following amine and dianhydride reactants:

| Diamine | Mol Ratio | Dianhydride | Mol Ratio | Inh. Visc. (dl/g) | Tg (°C.) |
|---|---|---|---|---|---|
| DABA | 0.65 | DCBTDA | 1.0 | 0.280 | — |
| DAPI | 0.35 | | | | |
| DABA | 0.75 | DCBTDA | 1.0 | 0.320 | — |
| DAPI | 0.25 | | | | |
| DD | 0.55 | DCBTDA | 0.9 | 1.120 | 374 |
| EMDDM | 0.45 | TXDA | 0.1 | | |
| DAPI | 1.0 | DCBTDA | 1.0 | 0.50 | 333 |
| DMB | 1.0 | DCBTDA | 1.0 | 0.190 | 307 |
| TSN | 1.0 | DCBTDA | 1.0 | 0.230 | 368 |
| DD | 0.55 | DCBTDA | 1.0 | 0.640 | 365 |
| EMDDM | 0.45 | | | | |
| DD | 0.55 | DCBTDA | 0.5 | 1.070 | 402.4 |
| EMDDM | 0.45 | BTDA | 0.5 | | |
| DD | 0.55 | DCBTDA | 0.1 | 0.980 | 356 |
| EMDDM | 0.45 | BTDA | 0.9 | | |
| DAPOL | 1.0 | DCBTDA | 1.0 | 0.120 | 354 |
| DABA | 0.7 | DCBTDA | 1.0 | 0.290 | — |
| DAPI | 0.3 | | | | |

DD = Durene diamine
EMDDM = 4,4′-diamino-3,3′-diethyl-5,5′-dimethyl-diphenylmethane
DMB = 3,5-diaminomethylbenzoate
TSN = di(ortho-toluidine) sulfone
DAPOL = 2,4-diaminophenol dihydrochloride
TXDA = 3,3′,4,4′-thioxanthone dianhydride Each of these polyimide systems exhibits solubility when tested according to the procedure in Example 3.

EXAMPLE 6

The indicated polyimide is dissolved in gamma-butyrol-actone in approximately 10% solids concentration. The solution is stirred overnight in the dark and then filtered through a 1 μm filter. A 4″ diameter silicon wafer is pretreated with adhesion promoter 3289/3290 (aminopropyl disiloxane solution in 95:5 ethanol/H$_2$O) from Ciba-Geigy Corp. Three ml of the above polyimide solution is deposited onto the wafer and then spun at 1000 to 4000 rpm for thirty seconds in order to obtain approximately a 1 μm film. The polymer is then baked for thirty minutes in a convection oven at 90° C. under nitrogen purge. The polyimide film is then exposed through a Detrics Optics series I multidensity resolution mask on a Oriel Exposure tool. This unit is fitted with a 500 watt mercury xenon lamp and quartz optics. The wafer is developed by spray techniques using developers 3311/3312 (gamma-butyrolactone/GBL-xylene) from Ciba-Geigy Corp. The relative photospeed is determined by noting the exposure energy required to effect first crosslink of the polymer sample (visual observation) and comparing this value to that required to reach the same degree of crosslinking with a standard polyimide product at the same film thickness. Lower exposure energies are indicative of increased photospeed.

The results are noted in the following table:

| Polyimide | Exposure Energy (mJ/cm$^2$) |
|---|---|
| Control | 120 |
| PI 4 in Ex. 5 | 141/45.1* |

| Polyimide | Exposure Energy (mJ/cm²) |
|---|---|
| PI 7 in Ex. 5 | 65.6/87.0 |
| PI 8 in Ex. 5 | 78.9/68.6 |
| PI 9 in Ex. 5 | 80.0/70.6 |

*second value indicates determination with filtering light of exposure apparatus through mercury line interference filter.

These data thus indicate the increased photospeeds in negative photoresists exhibited by the instant polyimides.

EXAMPLE 7

Positive Photoresist

A flask is charged with 9.5 grams of a polymer prepared (according to Ex. 2) from DAPI (25), DABA (75), DCBTDA (100), inh. visc. 0.31 dl/g, in 40.5 grams of gamma-butyrolactone (19% solids). The solution is then mixed with 1.425 grams of dissolution inhibitor THBP-215 diazo ester type 3.3 (trihydroxybenzophenone/diazo sulfonate ester) from ICI Americas. The solution is stirred overnight and then filtered through a 1 μm. Three ml of the solution are spun (3000 rpm) onto a 4" diameter silicon wafer which is pretreated with adhesion promoter 3289/3290 (aminopropyl disiloxane solution in 95:5 ethanol/H₂O) from Ciba-Geigy Corp. The resulting film is baked for ten minutes at 110° C. on a hot plate and then in a forced air oven at 90° C. for 30 minutes under nitrogen purge. The resulting film thickness is 1.2 μm. The wafer is exposed on an exposure tool (Oriel Corp.) using a 500 watt mercury xenon lamp, with an exposure energy of 50 mJ/cm² through a Dietrics Optics Resolution mask. The exposed wafer is dipped (developed) for 60 seconds in a mixture of 25% tetramethylammonium hydroxide solution (SB-312 developer from KTI Chemicals) and 75% of 18 megohm water. 5–10 μm line space pairs are resolved, an indication of high resolution.

In summary, this invention is seen to provide a class of polyimides exhibiting a broad range of improved performance characteristics. Variations may be made in proportions, procedures and materials without departing from the scope of the invention as defined in the following claims.

What is claimed is:

1. A polyimide of at least one aromatic tetracarboxylic dianhydride and at least one aromatic diamine which comprises 5 to 100 mol % of at least one structural element of the formula I

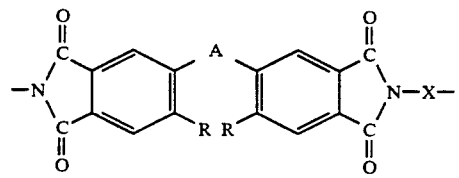
(I)

and 95 to 0 mol % of at least one structural element of the formula II

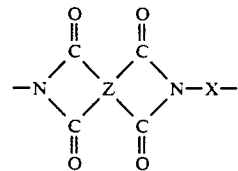
(II)

wherein A is a direct bond or A is

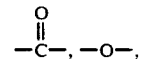

$-SO_2-$, or $C(CF_3)_2$;

R is independently halogen, OH, $OR_1$, $NO_2$, $COOR_1$, $CF_3$ or $(CF_2)_{1-4}CF_3$ and $R_1$ is $C_1-C_6$alkyl;

Z is an unsubstituted or substituted tetravalent radical to which in each case two carbonyl groups are bonded in the ortho- or peri-position with the proviso that Z is not

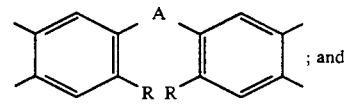
; and

X is the divalent radical or an aromatic diamine.

2. The polyimide of claim 1, wherein A is the direct bond or A is

$-O-$ or $-SO_2-$.

3. The polyimide of claim 2, wherein A is

4. The polyimide of claim 1, wherein R is halogen or methoxy.

5. The polyimide of claim 4, wherein R is chlorine.

6. The polyimide of claim 1, wherein said dianhydride is 2,2'-dichloro-4,4',5,5'-benzophenonetetracarboxylic acid dianhydride.

7. The polyimide of claim 1, wherein X is a divalent, mono- or polynuclear $C_6-C_{22}$ arylene radical.

8. The polyimide of claim 1, wherein X is a phenylene radical.

9. A polyimide according to claim 1, in which an aromatic radical X has the formulae III, IIIa or IIIb

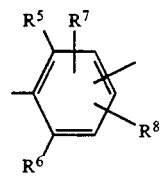
(III)

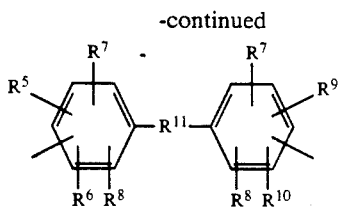

in which, in formula III, the free bonds are in the meta- or para-position relative to one another, in formula IIIa the free bonds are in the meta-or para-position relative to the $R^{11}$ group and $R^5$ and $R^6$ are bonded in the two ortho-positions of the free bond, and in formula IIIb the free bonds are in the 2-,3-,6- or 7-positions and $R^5$ and $R^6$ are in the two ortho-positions of the free bonds, $R^{11}$ is a direct bond or $R^{11}$ is —O—, —S—, —SS—, —SO—, —SO$_2$—, —CO—, —COO—, —NH—,

with 1 to 6 C atoms in the alkyl

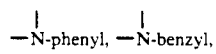

—CONH—, —CON-alkyl- with 1 to 6 C atoms in the alkyl, —CON-phenyl-, —CON-benzyl-,

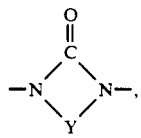

in which Y is

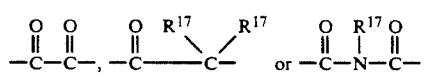

and $R^{17}$ is a hydrogen atom, $C_1$-$C_6$-alkyl or phenyl, linear or branched alkylene with 1 to 3 C atoms, alkylidene which has 2 to 12 C atoms and is unsubstituted by Cl or F, cycloalkylidene with 5 or 6 ring carbon atoms, phenylene, phenylenedioxy or the group

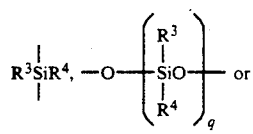

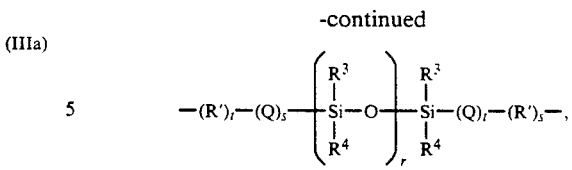

in which $R^3$ and $R^4$ are alkyl or alkoxy with 1 to 6 C atoms, phenyl, benzyl, phenoxy or benzyloxy, r is a number from 1 to 10, t is 0 or 1, s is 0 or 1, R' is —O— or —S—, Q is $C_1$-$C_6$-alkylene and q is a number from 1 to 100, $R^5$ and $R^6$ are alkyl or alkoxy with 1 to 12 C atoms, alkoxyalkyl with 2 to 12 C atoms, cyclopentyl, cyclohexyl or benzyl, or, in the formula III or IIIa $R^5$ and $R^7$ are bonded in adjacent positions and together are trimethylene or tetramethylene, in which case $R^6$ is hydrogen, alkyl or alkoxy with 1 to 12 C atoms, alkoxyalkyl with 2 to 12 C atoms, cyclopentyl, cyclohexyl or benzyl a hydrogen atom, or $R^7$ and $R^8$ are hydrogen atoms or independently have the meanings of $R^5$ and $R^6$, and $R^9$ and $R^{10}$ are hydrogen atoms or independently have the meanings of $R^5$ and $R^6$, or $R^7$ and $R^9$ in formula IIIa together are trimethylene or tetramethylene.

10. A polyimide according to claim 9, in which X in formula I is a radical of the formula

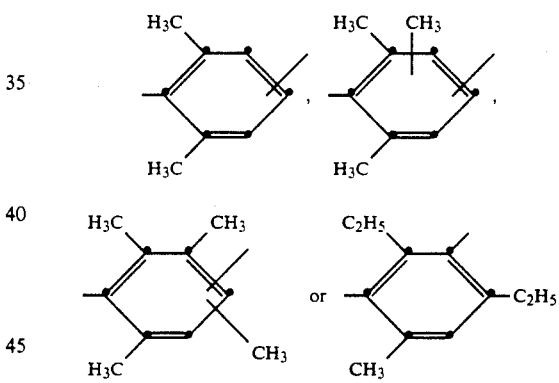

in which the free bonds are in the meta- or para-position relative to one another, or of the formula

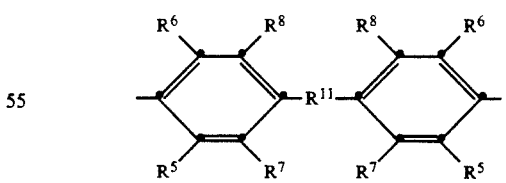

in which $R^5$ and $R^6$ independently of one another are methyl, ethyl, n-propyl or isopropyl, $R^7$ and $R^8$ are hydrogen atoms or have the meaning of $R^5$, or $R^5$ and $R^7$ together are trimethylene or tetramethylene and $R^6$ and $R^8$ are hydrogen atoms, and $R^{11}$ is a direct bond or $R^{11}$ CH$_2$ or CO.

11. A polyimide according to claim 1, in which x has the formula

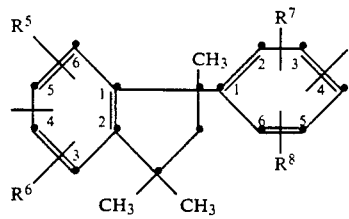

in which R⁵, R⁶, R⁷ and R⁸ are hydrogen or one free bond is in the 4'- or 5'-position and the other is in the 3-, 4- or 5-position and R⁵ and R⁶ or R⁷ and R⁸ are in the ortho-positions of the free bond and are alkyl or alkoxy with 1 to 12 C atoms or alkoxyalkyl with 2 to 12 C atoms.

12. A polyimide according to claim 1, in which Z is

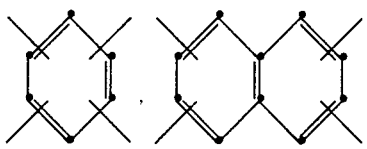

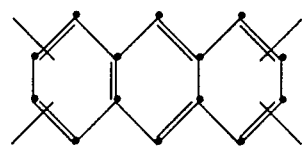

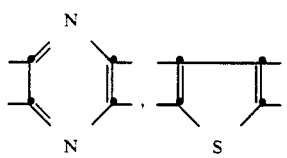

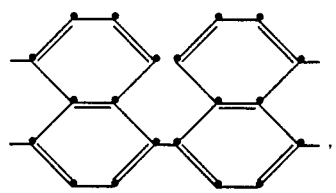

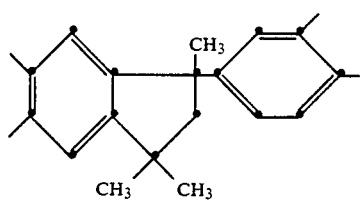

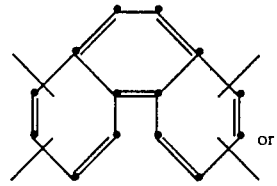 or

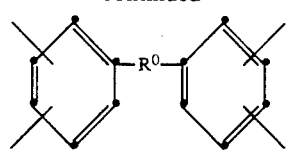

in which $R^o$ is a direct bond or $R^o$ is a bridge group of the formula

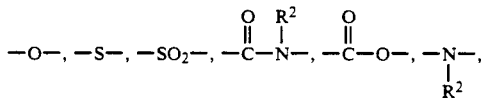

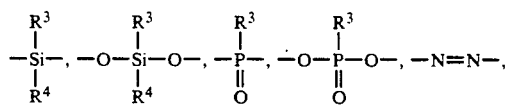

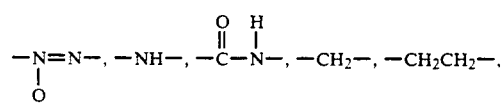

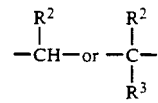

in which $R^2$, $R^3$ and $R^4$ are alkyl with 1 to 6 C atoms, phenyl or benzyl, and $R^3$ and $R^4$ are also alkoxy with 1 to 6 C atoms, phenoxy or benzyloxy.

13. A polyimide according to claim 12, in which Z is a radical of the formula

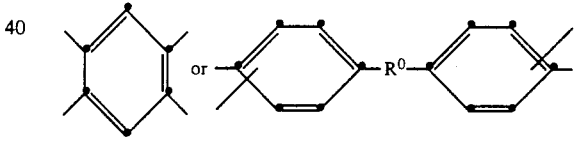

in which $R^o$ is a direct bond or $R^o$ —O—, —SO₂—, —CH₂— or —CO—.

14. A polyimide according to claim 13, in which Z is a radical of the formula

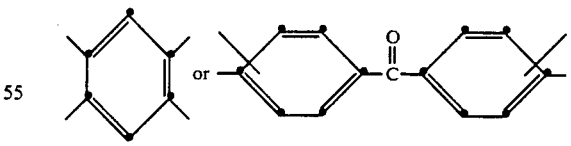

or mixtures thereof.

15. A polyimide according to claim 1 which contains 100 mol % of structural elements of the formula I.

16. The polyimide of claim 15, wherein A is

and each R is chlorine.

17. The polyimide of claim 16, wherein X is a mixture of the divalent radicals from diaminophenylindane and 3,5-diaminobenzoic acid.

18. The polyimide according to claim 1 which contains elements of both formula (I) and formula (II).

19. The polyimide of claim 18, wherein A is

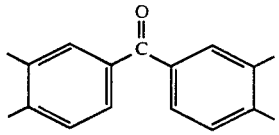

each R is chlorine and Z is

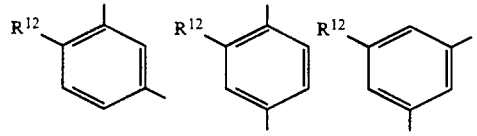

20. A process for the preparation of polyimides according to claim 1, which comprises subjecting at least one compound of the formula (I) of claim 1 or at least one compound of the formula I of claim 1 together with at least one tetracarboxylic dianhydride of the formula

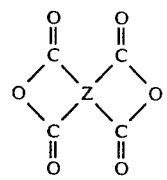

to a polycondensation reaction with at least one diamine of the formula $H_2N-X-NH_2$, when X and Z are as defined in claim 1, and then cyclizing the formed polyamide acid with heat or heat and a dehydrating agent.

21. A coated substrate comprising a carrier material onto which a coating of polyimide according to claim 1 is applied.

22. The coated substrate of claim 21, wherein said polyimide contains at least 30 mol % of a divalent radical derived from aromatic diamines containing acidic or phenolic functionalities and an effective dissolution inhibiting amount of a dissolution inhibitor for said polyimide.

23. A polyimide according to claim 7, wherein X is a radical of the formula

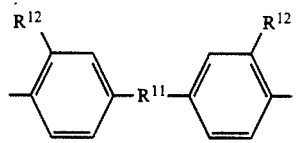

wherein $R^{11}$ is a direct bond, —O—, —CO— or —CH$_2$— and $R^{12}$ is hydrogen, methyl, ethyl, isopropyl, methoxy, hydroxy or carboxy.

* * * * *